United States Patent [19]

DeMarinis

[11] 4,058,609
[45] Nov. 15, 1977

[54] 7-DITHIOACETAMIDO CEPHALOSPORINS

[75] Inventor: Robert M. DeMarinis, King of Prussia, Pa.

[73] Assignee: SmithKline Corporation, Philadelphia, Pa.

[21] Appl. No.: 700,290

[22] Filed: June 28, 1976

[51] Int. Cl.$^2$ ............... A61K 31/545; C07D 501/50; C07D 501/28

[52] U.S. Cl. ............... 424/246; 260/526 S; 260/539 R; 260/465.1; 544/21; 544/26; 544/29

[58] Field of Search ............... 260/243 C; 424/246

[56] References Cited

U.S. PATENT DOCUMENTS

| | | | |
|---|---|---|---|
| 3,828,037 | 8/1974 | DeMarinis et al. | 260/243 C |
| 3,883,520 | 5/1975 | DeMarinis | 260/243 C |
| 3,884,915 | 5/1975 | DeMarinis et al. | 260/243 C |
| 3,920,639 | 11/1975 | Dolfini | 260/243 C |

OTHER PUBLICATIONS

Lewis et al., Antimicrobial Agents & Chemotherapy (1968), pp. 109–114 (1969).
Tsushima et al., Chemical Abstracts, 83 179084u (1975).

*Primary Examiner*—Nicholas S. Rizzo
*Assistant Examiner*—Diana G. Rivers
*Attorney, Agent, or Firm*—Joseph A. Marlino; Richard D. Foggio; William H. Edgerton

[57] ABSTRACT

Novel cephalosporins having a dithioacetamido substituent at the 7-position are prepared. These compounds have antibacterial activity.

10 Claims, No Drawings

7-DITHIOACETAMIDO CEPHALOSPORINS

This invention relates to cephalosporin compounds which have antibacterial activity. In particular, the invention relates to compounds having a dithioacetamido substituent at position 7 of the cephem nucleus.

The cephalosporin antibiotics of this invention are represented by the following formula:

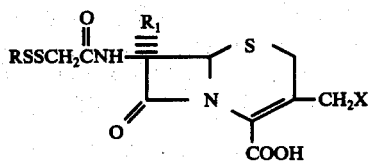

FORMULA I where:
R is lower alkyl of from 1 to 4 carbon atoms, trichloromethyl, trifluoromethyl, cyanomethyl, or trifluoroethyl;

$R_1$ is hydrogen or methoxy;

X is hydrogen, acetoxy of SHet and Het is a 5 or 6 membered heterocyclic ring containing carbon and 1 to 4 atoms selected from the group comprising N, O and sulfur, unsubstituted or substituted with one or two substituents comprising lower alkyl of from 1 to 4 carbons, mercapto, trifluoromethyl or $(CH_2)_n COX$ where $n$ is 0 to 5 and X is —OH or —$NH_2$.

Particular compounds of formula I are those where Het is unsubstituted or methyl substituted triazolyl, tetrazolyl, oxazolyl, oxadiazolyl, thiazolyl or thiadiazolyl and R is methyl.

Included within the scope of this invention are the non-toxic pharmaceutically acceptable salts that are formed by the reaction of the cephalosporanic acid with a pharmaceutically acceptable base. Many salts and methods of preparation are known within the art. These include alkali metal salts such as sodium or potassium and ammonium salts including organic amines such as triethylamine and the like.

Further, included within the scope of this invention are hydrates and alcoholates which are formed from the acid.

The compounds of the invention are prepared by appropriate acylation of a 7-aminocephalosporanic acid or a derivative thereof. A standard removable ester, such as the t-butyl ester, may also be employed as a starting material in place of the free acid. Common methods to activate the carboxyl group, such as mixed anhydride, acid halide or activated ester are known to one skilled in the art and may be used. Further, a coupling reagent such as dicyclohexylcarbodiimide or N,N'-carbonyldiimidazole may be used to acylate 7-aminocephalosporanic acid esters and derivatives thereof.

The 7-aminocephalosporanic acids and derivatives and methods for their preparation are well known in the cephalosporin art. General methods to prepare these compounds are in the book *Cephalosporins and Penicillins-Chemistry and Biology*, ed. Flynn, Academic Press, New York, 1972. Methods to prepare the 7-amino-3-heterocyclicthiomethyl compounds are given in U.S. Pat. No. 3,516,997.

The compounds of this invention have broad spectrum antibacterial activity with minimum inhibitory concentrations (MIC) ranging from 0.2 to >200 ug/ml when determined by standard agar inclusion methods. Table 1 shows MIC's for a variety of compounds within the scope of this invention against representative Gram-positive and Gram-negative bacteria.

TABLE 1

| | MIC μg/ml | | | | |
|---|---|---|---|---|---|
| | Test Compound * | | | | Cefazolin |
| Test Bacteria | A | B | C | D | E |
| *S. aureus* HH127 | 0.4 | 3.1 | 3.1 | 0.2 | 0.4 |
| *S. aureus* SK23390 | 0.4 | 3.1 | 3.1 | 0.2 | 0.4 |
| *S. aureus* Villaluz | 6.3 | 50 | 6.3 | 3.1 | 25 |
| *Strep. faecalis* HH34358 | 12.5 | 50 | 50 | 12.5 | 6.3 |
| *E. coli* SK12140 | 3.1 | 12.5 | 12.5 | 6.3 | 1.6 |
| *E. coli* HH33779 | 6.3 | 100 | 25 | 12.5 | 3.1 |
| *Kleb. pneumo.* SK4200 | 3.1 | 12.5 | 6.3 | 3.1 | 3.1 |
| *Kleb. pneumo.* SK1200 | 0.8 | 6.3 | 3.1 | 3.1 | 0.8 |
| *Salmonella paratyphi* ATCC12176 | 0.8 | 6.3 | 6.3 | 6.3 | 1.6 |
| *Shegella paradysenteriae* HH117 | 0.8 | 12.5 | 3.1 | 1.6 | 0.8 |
| *Pseudo aeruginosa* HH63 | >200 | >200 | >100 | >200 | >200 |
| *Serratia marc.* ATCC13880 | >200 | >200 | >100 | >200 | >200 |
| *Proteus morgani* 179 | >200 | >200 | >100 | >200 | >200 |
| *Entero. aerogenes* 13048 | 3.1 | 100 | 100 | 25 | 1.6 |
| *Entero. cloacae* HH31254 | 1.6 | 12.5 | 12.5 | 25 | 0.8 |

*See Table 2 for structures

TABLE 2

| Compound | R | $R_1$ | X |
|---|---|---|---|
| A | methyl | hydrogen | 1-methyltetrazol-5-ylthio |
| B | trichloromethyl | hydrogen | 1-methyltetrazol-5-ylthio |
| C | trifluoromethyl | hydrogen | 1-methyltetrazol-5-ylthio |
| D | methyl | hydrogen | acetoxy |

The novel compounds of this invention are administered parenterally in conventional injectable dosage unit forms to achieve antibacterial activity. The appropriate dose of the compound of Formula I is incorporated with carriers according to accepted pharmaceutical practices. The dithioacetamido cephalosporin derivatives will be present in an amount to produce antibacterial activity. A single dosage unit will be in the range of from about 100 mg. to about 1000 mg. Equally divided daily doses are administered to provide an active daily dose selected from 250 mg. to 6.0 g. The dosages are dependent upon the age and weight of the subject and on the infection being treated. The dosage can be determined by those skilled in the art based on data disclosed herein and experience with known cephalosporins.

The pharmaceutical carrier employed may be, for example, sterile water for injection, bacteriostatic water for injection or sodium chloride injection. The amount of carrier or diluent employed will vary depending on the amount of compound to be reconstituted.

The following examples illustrate the preparation of specific cephalosporin compounds having antibacterial activity. However, this should not be construed as a limitation of the invention since other variations will be obvious to those skilled in the art.

EXAMPLE 1

To 80 ml. of dimethylsulfide and 40 ml. of triethylamine was added dropwise 20 g. of mercaptoacetic acid with stirring. The reaction was stirred at room temperature for two hours and added to 700 ml. of water and extracted with 300 ml. of chloroform. The aqueous phase was adjusted to pH 1 with 6 N sulfuric acid and extracted with 300 ml. of ethyl acetate. The ethyl acetate extracts were washed with water, dried over magnesium sulfate, filtered and concentrated to yield methyldithioacetic acid.

2.2 g. of methyldithioacetic acid and 6.1 g. of t-butyl 7-amino-3-(1-methyltetrazol-5-ylthiomethyl)-3-cephem-4-carboxylate were dissolved in 100 ml. tetrahydrofuran, cooled and treated dropwise with 3.3 g. of dicyclohexylcarbodiimide in 50 ml. of tetrahydrofuran. The reaction mixture was stirred at room temperature overnight and filtered. The filtrate was evaporated to dryness to yield t-butyl 7-methyldithioacetamido-3-(1-methyltetrazol-5-yl-thiomethyl)-3-cephem-4-carboxylate.

To 4.7 g. of the t-butyl ester in 25 ml. of dimethoxybenzene was added 25 ml. of trifluoroacetic acid and the reaction was stirred at room temperature for two hours. The trifluoroacetic acid was evaporated and the product was precipitated with 300 ml. of ether to give crude 7-methyldithioacetamido-3-(1-methyltetrazol-5-yl-thiomethyl)-3-cephem-4-carboxylic acid. This was dissolved in methanol and treated with 10 ml. of sodium 2-ethylhexanoate (30% in isopropanol) and the salt precipitated by the dropwise addition of ether. The precipitated salt was collected, and dried overnight under vacuum to yield 7-methyldithioacetamido-3-(1-methyltetrazol-5-yl-thiomethyl)-3-cephem-4-carboxylic acid, sodium salt hydrate which decomposes at >155° C.

EXAMPLE 2

Employing the above procedure and substituting t-butyl 7β-amino-7α-methoxy-3-(1-methyltetrazol-5-ylthiomethyl)-3-cephem-4-carboxylate for the starting ester yields 7β-methyl-dithioacetamido-7α-methoxy-3-(1-methyltetrazol-5-yl-thiomethyl)-3-cephem-4-carboxylic acid.

EXAMPLE 3

To 18.6 g. of a stirred solution of ice cold trichloromethylsulfenyl chloride was added dropwise 9.2 g. of mercaptoacetic acid. The reaction mixture was stirred at 5°-10° C. for 1 hour and then allowed to come to room temperature where it was stirred an additional 3-4 hours and allowed to stand overnight to yield crude trichloromethyldithioacetic acid. The crude acid was chromatographed on 10 g. of silica gel eluting with 2% methanol chloroform to give with the first fraction a yellow viscous oil, which solidified at room temperature.

In like manner using the procedure of Example 1, t-butyl 7-amino-3-(1-methyltetrazol-5-ylthiomethyl)-3-cephem-4-carboxylate was reacted with the above trichloro acid to yield 7-(trichloromethyldithioacetamido)-3-(1-methyltetrazol-5-ylthiomethyl)-3-cephem-4-carboxylic acid.

EXAMPLE 4

20.0 g. of trifluoromethylsulfenyl chloride was cooled in a dry ice-isopropanol bath and added to 200 ml. of ether in a dry ice-isopropanol bath. The dry ice-isopropanol bath was replaced by an ice bath and the solution stirred while 6.89 g. of mercaptoacetic acid was added in portions. Then the addition was completed the reaction was stirred in the ice bath for one hour and then at room temperature for two hours. The ether was evaporated to yield trifluoromethyldithioacetic acid as a colorless liquid.

A mixture of thionyl chloride (2.70 g.) and trifluoromethyldithioacetic acid (2.88 g.) was stirred and heated to 45°-50° C. for 4 hours. The reaction was concentrated under reduced pressure to yield trifluoromethyldithioacetyl chloride.

The acid chloride was dissolved in 10 ml. of methylene chloride and added dropwise to a suspension of 5.79 g. of t-butyl 7-amino-3-(1-methyltetrazol-5-ylthiomethyl)-3-cephem-4-carboxylate and 0.60 g. of magnesium oxide in 50 ml. of methylene chloride. The reaction was stirred at 0°-10° C. and filtered. The filter cake was washed with chloroform and the filtrate washed with dilute hydrochloric acid water and dried. The filtrate was concentrated under reduced pressure and mixed with petroleum ether with stirring. The solid was collected, washed with petroleum ether and dried to yield t-butyl 7-(trifluoromethyldithioacetamido)-3-(1-methyltetrazol-5-ylthiomethyl)-3-cephem-4-carboxylate.

The t-butyl ester was converted to the corresponding carboxylic acid by the procedure set forth in Example 1.

EXAMPLE 5

Employing the procedure outlined in Example 1, the following t-butyl 7-amino-3-heterocyclicthiomethyl-3-cephem-4-carboxylates are employed as the starting material which upon removal of the protecting group yield the corresponding 7-dithioacetamido-3-heterocyclicthiomethyl-3-cephem-4-carboxylic acids.

t-butyl 7-amino-3-(tetrazol-5-ylthiomethyl)-3-cephem-4-carboxylate t-butyl 7-amino-3-(1,3,4-thiadiazol-2-ylthiomethyl)-3-cephem-4-carboxylate t-butyl 7-amino-3-(5-trifluoromethyl-1,3,4-thiadiazol-2-ylthiomethyl)-3-cephem-4-carboxylate t-butyl 7-amino-3-(5-ethyl-1,3,4-thiadiazol-2-ylthiomethyl)-3-cephem-4-carboxylate t-butyl 7-amino-3-(5-mercapto-1,3,4-thiadiazol-2-ylthiomethyl)-3-cephem-4-carboxylate t-butyl 7-amino-3-(3-methylthio-1,2,4-thiadiazol-5-ylthiomethyl)-3-cephem-4-carboxylate t-butyl 7-amino-3-(1,2,4-triazol-3-ylthiomethyl)-3-cephem-4-carboxylate t-butyl 7-amino-2-(5-methyl-1,2,4-triazol-3-ylthiomethyl)-3-cephem-4-carboxylate t-butyl 7-amino-3-(4-methyl-5-trifluoromethyl-1,2,4-triazol-3-ylthiomethyl)-3-cephem-4-carboxylate t-butyl 7-amino-3-(5-hydroxy-4-methyl-1,2,4-triazol-3-ylthiomethyl)-3-cephem-4-carboxylate t-butyl 7-amino-3-(thiazol-5-ylthiomethyl)-3-cephem-4-carboxylate t-butyl 7-amino-3-(4-methylthiazol-5-ylthiomethyl)-3-cephem-4-carboxylate t-butyl 7-amino-3-(1,3,4-oxadiazol-2-ylthiomethyl)-3-cephem-4-carboxylate t-butyl 7-amino-3-(5-methyl-1,3,4-oxadiazol-2-ylthiomethyl)-3-cephem-4-carboxylate t-butyl 7-amino-3-(oxazol-5-ylthiomethyl)-3-cephem-4-carboxylate

EXAMPLE 6

A solution of 4.14 g. (0.3 mol) of methyldithioacetic acid (as prepared in Example 1) and 3.45 g. (0.03 mol) of N-hydroxysuccinimide in 50 ml. of tetrahydrofuran was stirred and cooled to 0° C. and 6.2 g. of dicyclohexylcarbodiimide was added and the reaction mixture was stirred at 0° C. for 1 hour and then at 25° C. for 12 hours. The precipitate was collected, washed with tetrahydrofuran, then dissolved in ether and the solution decolorized with charcoal and filtered. The filtrate was evaporated to give the activated ester N-hydroxysuccinimidyl methyldithioacetate.

To 4.35 g. of 7-aminocephalosporanic acid (7-ACA) and 3 g. of triethylamine in 75 ml. of dimethylformamide was added 3.76 g. of the activated ester and the reaction stirred for 1 hour. The mixture was evaporated to dryness and water and ethyl acetate were added. The layers were separated and fresh ethyl acetate was added to the aqueous phase. The mixture was acidified pH 2.5 with 3 N hydrochloric acid, filtered, the layers separated and the aqueous phase extracted twice with ethyl acetate. The extracts were washed with water, dried, filtered and concentrated to yield 7-(methyldithioacetamido)-cephalosporanic acid.

The residue was dissolved in 20 ml. of methanol and a 5% solution of sodium methoxide in methanol was added until the pH reached 6.9. Ether (400 ml) was added with stirring and the precipitate was collected, washed with ether and dried to give the sodium salt of the above cephalosporanic acid.

EXAMPLE 7

Following the procedure outlined in Example 6, cyanomethyldithioacetic acid is reacted with N-hydroxysuccinimide to yield 7-(cyanomethyldithioacetamido)-cephalosporanic acid.

EXAMPLE 8

Similarly using the procedure set forth in Example 6, 3.83 g. of 7-amino-3-[1-(2-carbamoylethyl)tetrazol-5-ylthiomethyl)]-3-cephem-4-carboxylic acid and 3.86 g. of 7-amino-3-[1-(2-carboxyethyl)tetrazol-5-ylthiomethyl)]-3-cephem-4-carboxylic acid used as starting materials yields the corresponding 7-methyldithioacetamido derivatives.

EXAMPLE 9

Employing the procedure outlined in Example 6, and using 7-aminodesacetoxycephalosporanic acid (7-ADCA) as a starting material in place of 7-ACA yields 7-(methyldithioacetamido)-3-methyl-3-cephem-4-carboxylic acid.

EXAMPLE 10

A sterile injectable solution is prepared by reconstituting 7-methyldithioacetamido-3-(1-methyltetrazol-5-yl-thiomethyl)-3-cephem-4-carboxylic acid, sodium salt as follows:

| Vial Size | Sterile Water For Injection | Average Concentration |
| --- | --- | --- |
| 250 mg. | 2.0 ml | 125 mg/ml |
| 500 mg. | 2.0 ml | 225 mg/ml |
| 1 gram | 2.5 ml | 330 mg/ml |

Shake well until the compound is dissolved. A volume equivalent to 500 mg. of the active ingredient is injected intramuscularly every 6 hours.

What is claimed is:

1. A chemical compound of the formula:

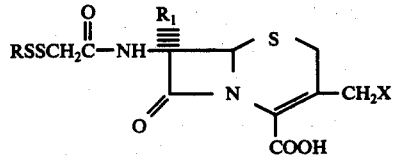

or a non-toxic pharmaceutically acceptable salt thereof in which:
R is lower alkyl of from 1–4 carbon atoms, trichloromethyl, trifluoromethyl, cyanomethyl, or trifluoroethyl;
$R_1$ is hydrogen or methoxy;
X is SHet; and
Het is triazolyl, tetrazolyl, oxazolyl, oxadiazolyl, thiazolyl or thiadiazolyl unsubstituted or substituted with one or two substituents comprising lower alkyl of 1 to 4 carbons, mercapto, trifluoromethyl or $(CH_2)_nCOX$ where n is 0 to 5 and X is OH or $NH_2$.

2. A chemical compound in accordance with claim 1 in which R is lower alkyl.

3. A chemical compound in accordance with claim 2 in which Het is tetrazolyl, thiadiazolyl, triazolyl or oxidiazolyl unsubstituted or substituted with one or two substituents selected from the group consisting of lower alkyl of from 1 to 4 carbons, mercapto, trifluoromethyl or $(CH_2)_nCOX$ where n is 0 to 5 and X is OH or $NH_2$.

4. A chemical compound in accordance with claim 3 in which Het is tetrazolyl substituted with lower alkyl of from 1 to 4 carbons.

5. A chemical compound in accordance with claim 4 in which lower alkyl is methyl.

6. A compound in accordance with claim 5 being the compound 7-methyldithioacetamido-3-(1-methyltetrazol-5-ylthiomethyl)-3-cephem-4-carboxylic acid.

7. A pharmaceutical composition in dosage unit form having antibacterial activity comprising a pharmaceutical carrier and a chemical compound as defined in claim 1.

8. A pharmaceutical composition in dosage unit form having antibacterial activity comprising a pharmaceutical carrier and a chemical compound as defined in claim 6.

9. The method of producing antibacterial activity which comprises administering parenterally to animals requiring said treatment an amount sufficient to produce said activity a chemical compound as defined in claim 1.

10. The method of producing antibacterial activity which comprises administering parenterally to animals requiring said treatment a dosage unit of from about 100 mg. to about 1000 mg. of a chemical compound as defined in claim 1.

* * * * *